(12) United States Patent
Sohn et al.

(10) Patent No.: US 9,282,892 B2
(45) Date of Patent: Mar. 15, 2016

(54) METHOD AND APPARATUS FOR DISPLAYING BIO-INFORMATION

(75) Inventors: Jun-il Sohn, Yongin-si (KR); Yoon-seo Koo, Seoul (KR); Hong-sig Kim, Seongnam-si (KR); Kyoung-ho Kang, Hwaseong-si (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 927 days.

(21) Appl. No.: 12/685,233

(22) Filed: Jan. 11, 2010

(65) Prior Publication Data
US 2010/0179394 A1 Jul. 15, 2010

(30) Foreign Application Priority Data

Jan. 14, 2009 (KR) .................. 10-2009-0002976

(51) Int. Cl.
| | |
|---|---|
| *A61B 5/00* | (2006.01) |
| *G06F 19/00* | (2011.01) |
| *A61B 5/01* | (2006.01) |
| *A61B 5/021* | (2006.01) |
| *A61B 5/024* | (2006.01) |
| *A61B 5/0402* | (2006.01) |
| *A61B 5/145* | (2006.01) |

(52) U.S. Cl.
CPC . *A61B 5/00* (2013.01); *A61B 5/743* (2013.01); *G06F 19/3406* (2013.01); *G06F 19/3487* (2013.01); *A61B 5/01* (2013.01); *A61B 5/021* (2013.01); *A61B 5/024* (2013.01); *A61B 5/0402* (2013.01); *A61B 5/145* (2013.01)

(58) Field of Classification Search
CPC ................. A61B 5/0002; G06F 19/30–19/366

USPC ......... 600/300–301, 481, 500–502, 515–519, 600/529, 509, 921, 485, 549; 128/920–925; 340/500–502, 506, 539.1, 340/539.11–539.19, 539.2, 539.21–539.29, 340/539.3, 539.31–539.32, 540–542, 544, 340/545.1, 546, 545.2, 547, 545.3, 545.4, 340/565

See application file for complete search history.

(56) References Cited

U.S. PATENT DOCUMENTS

| 5,262,944 A | * | 11/1993 | Weisner et al. ............... 600/300 |
| 5,464,012 A | * | 11/1995 | Falcone ....................... 600/301 |
| 5,473,536 A | | 12/1995 | Wimmer |

(Continued)

FOREIGN PATENT DOCUMENTS

| JP | 04-105640 A | 4/1992 |
| JP | 08-103415 A | 4/1996 |

(Continued)

OTHER PUBLICATIONS

Korean Office Action for Korean Patent Application No. 10-2009-0002976 dated Jan. 23, 2015.

*Primary Examiner* — William Thomson
*Assistant Examiner* — Marie Archer
(74) *Attorney, Agent, or Firm* — Cantor Colburn LLP

(57) ABSTRACT

A method of displaying bio-information on a screen includes outputting basic bio-information of a plurality of bio-parameters indicating a condition of a patient on one display screen, determining an occurrence of an event related to the plurality of bio-parameters, converting the basic bio-information into detailed bio-information about one of the plurality of bio-parameters based on a result of the determining an occurrence of an event, and outputting the converted detailed bio-information on the one display screen.

15 Claims, 11 Drawing Sheets

(56) References Cited

U.S. PATENT DOCUMENTS

| | | | |
|---|---|---|---|
| 5,482,050 A * | 1/1996 | Smokoff et al. | 600/523 |
| 5,640,953 A | 6/1997 | Bishop et al. | |
| 6,609,146 B1 * | 8/2003 | Slotznick | 709/200 |
| 6,707,476 B1 | 3/2004 | Hochstedler | |
| 6,988,989 B2 * | 1/2006 | Weiner et al. | 600/300 |
| 7,639,145 B2 * | 12/2009 | Lawson et al. | 340/573.1 |
| 2002/0177758 A1 * | 11/2002 | Schoenberg et al. | 600/300 |
| 2003/0135087 A1 * | 7/2003 | Hickle et al. | 600/26 |
| 2004/0054261 A1 * | 3/2004 | Kamataki et al. | 600/300 |
| 2006/0229557 A1 * | 10/2006 | Fathallah et al. | 604/131 |
| 2007/0049805 A1 * | 3/2007 | Schillizzi et al. | 600/300 |
| 2007/0271115 A1 | 11/2007 | Baldus et al. | |
| 2008/0270080 A1 * | 10/2008 | Zong | 702/188 |
| 2008/0281168 A1 * | 11/2008 | Gibson et al. | 600/301 |
| 2008/0319275 A1 * | 12/2008 | Chiu et al. | 600/300 |
| 2009/0054743 A1 * | 2/2009 | Stewart | 600/301 |
| 2009/0149723 A1 * | 6/2009 | Krauss et al. | 600/301 |
| 2010/0081891 A1 * | 4/2010 | Wang et al. | 600/301 |
| 2010/0113909 A1 * | 5/2010 | Batchelder et al. | 600/364 |

FOREIGN PATENT DOCUMENTS

| | | |
|---|---|---|
| JP | 2002-263070 A | 9/2002 |
| JP | 2004-194996 A | 7/2004 |
| JP | 2007-021213 A | 2/2007 |
| JP | 2007-330704 A | 12/2007 |
| KR | 1020050042964 A | 5/2005 |
| WO | WO 2008088843 A1 * | 7/2008 |

* cited by examiner

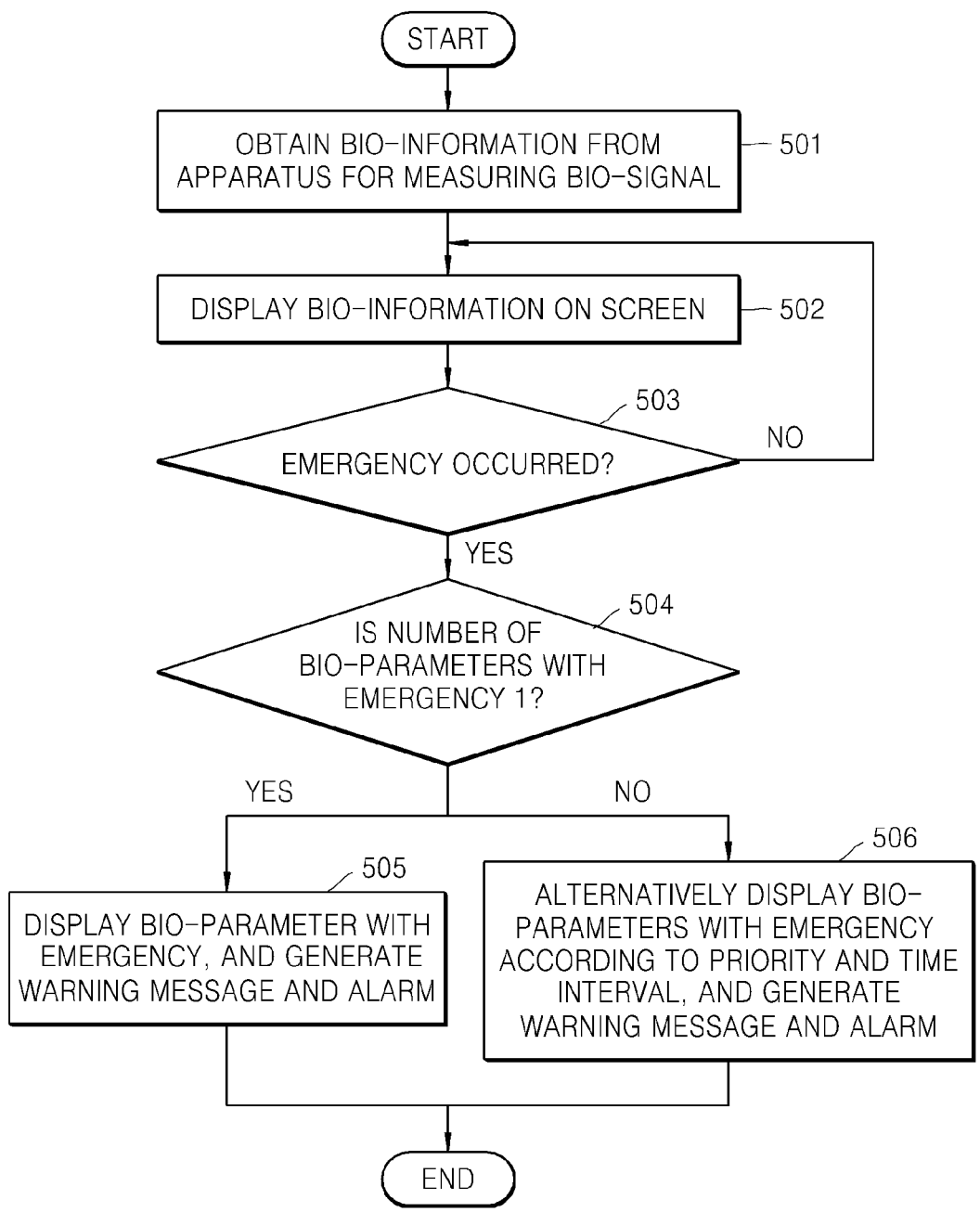

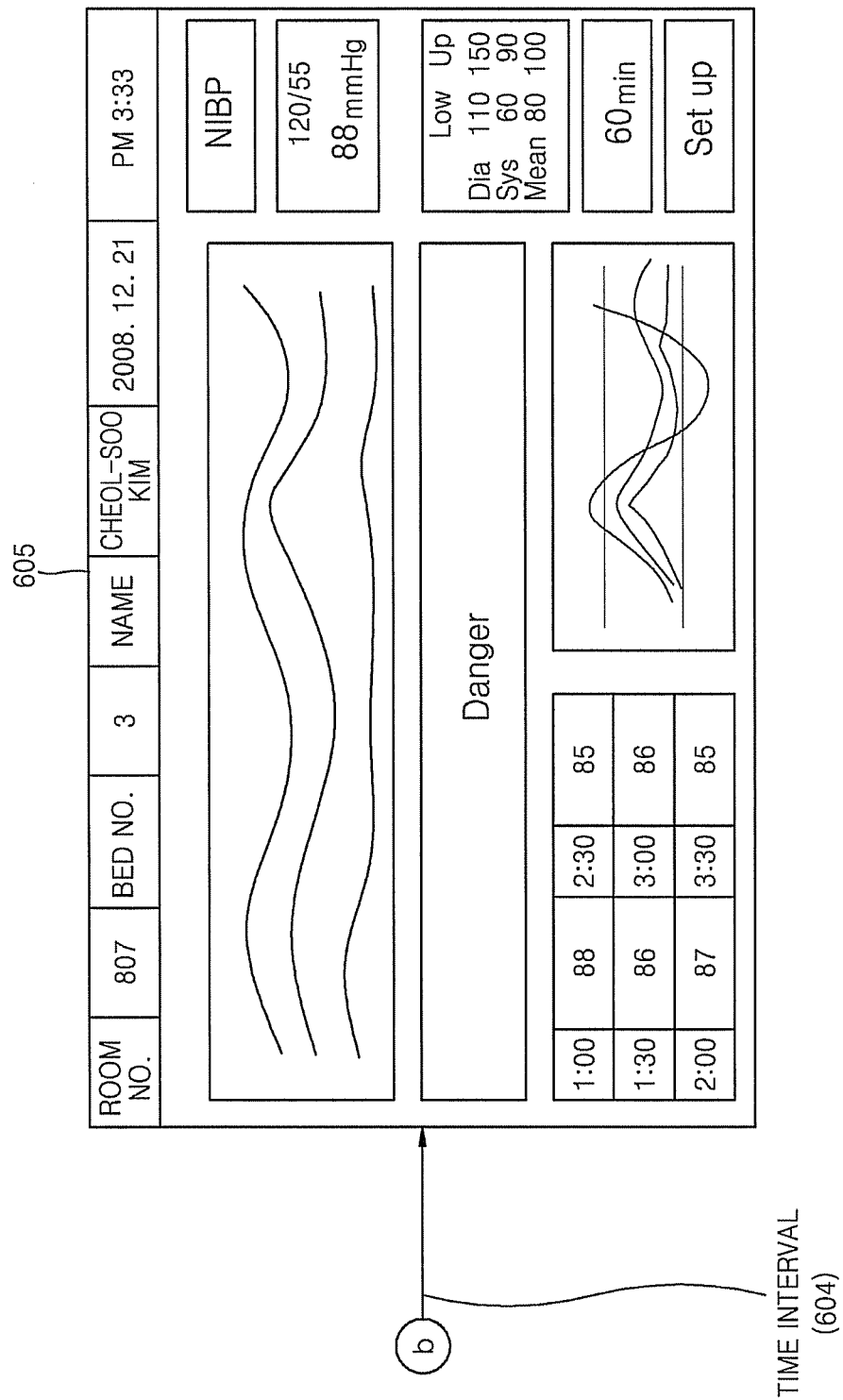

METHOD AND APPARATUS FOR DISPLAYING BIO-INFORMATION

CROSS-REFERENCE TO RELATED APPLICATIONS

This application claims priority to Korean Patent Application No. 10-2009-0002976, filed on Jan. 14, 2009, and all the benefits accruing therefrom under 35 U.S.C. §119, the disclosure of which is incorporated herein in its entirety by reference.

BACKGROUND

1. Field

Provided is a method and apparatus for displaying bio-information.

2. Description of the Related Art

The patient management market in the United States of America ("USA") is worth almost thirty billion dollars. A worldwide patient monitoring device market including the USA, is rapidly growing according to an increase in aging populations and in patients who need continuous monitoring, and according to technical development of wireless remote monitoring devices. Such circumstances also apply to other advanced countries and developing countries. A patient monitoring device continuously monitors values of bio-signals of a patient, such as temperature, heart rate, blood pressure, an electrocardiogram ("ECG"), and oxygen saturation.

SUMMARY

Provided is a method and apparatus for displaying bio-information to a user, to be easily understood by the user, and for quickly determining a condition of the user and emergent bio-information when an emergency occurs.

Provided is a computer readable recording medium including recorded thereon a program of computer executable instructions for executing the above method for displaying bio-information to a user.

Additional aspects will be set forth in part in the description which follows and, in part, will be apparent from the description, or may be learned by practice of the provided method, apparatus and computer readable recording medium.

Provided is a method of displaying bio-information, the method including outputting basic bio-information of a plurality of bio-parameters indicating a condition of a patient, on one display screen, determining an occurrence of an event related to the plurality of bio-parameters, converting the basic bio-information to detailed bio-information of one of the plurality of bio-parameters based on a result of the determining an occurrence of an event, and outputting the detailed bio-information on the one display screen.

Provided is a computer readable recording medium including recorded thereon, a program of computer executable instructions for executing a method of displaying bio-information.

Provided is an apparatus for displaying bio-information, the apparatus including a display unit which outputs basic bio-information of a plurality of bio-parameters, on one display screen, and a monitoring unit which determines an occurrence of an event related to the plurality of bio-parameters. The display unit converts the basic bio-information outputted on the one display screen into detailed bio-information of one of the plurality of bio-parameters, according to a result of the determining an occurrence of an event, and outputs the detailed bio-information on the one display screen.

BRIEF DESCRIPTION OF THE DRAWINGS

The above and/or other features of the invention will become apparent and more readily appreciated from the following description, taken in conjunction with the accompanying drawings of which:

FIG. 5 is a flowchart illustrating an exemplary embodiment of a method of converting a bio-information display screen when an emergency occurs;

FIGS. 6A-C are diagrams for describing an exemplary embodiment of a bio-information display screen conversion of a display unit.

DETAILED DESCRIPTION

Reference will now be made in detail to exemplary embodiments, of which are illustrated in the accompanying drawings. In this regard, the exemplary embodiments may have different forms and should not be construed as being limited to the descriptions set forth herein. Accordingly, the exemplary embodiments are merely described below, by referring to the figures, to explain features of the invention.

Like numbers refer to like elements throughout. As used herein, the term "and/or" includes any and all combinations of one or more of the associated listed items.

It will be understood that, although the terms first, second, third, etc., may be used herein to describe various elements, components, regions and/or sections, these elements, components, regions and/or sections should not be limited by these terms. These terms are only used to distinguish one element, component, region or section from another region or section. Thus, a first element, component, region or section discussed below could be termed a second element, component, region or section without departing from the teachings of the invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the invention will be described in detail with reference to the accompanying drawings.

Figure 1:
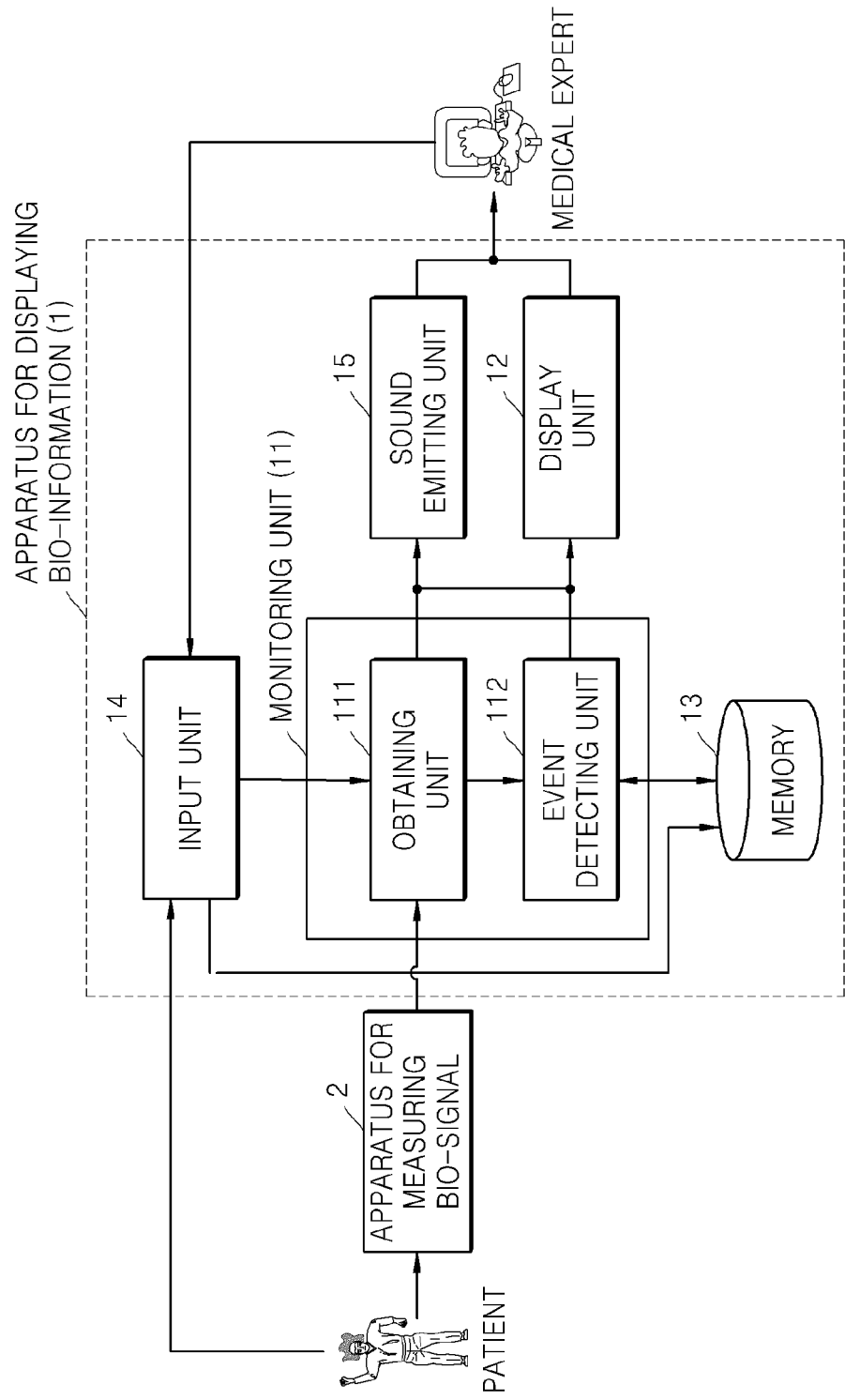
FIG. 1 is a block diagram of an exemplary embodiment of a system for displaying bio-information.

FIG. 1 is a block diagram of an exemplary embodiment of a system for displaying bio-information. Referring to FIG. 1, the system includes an apparatus 1 for displaying bio-information, and an apparatus 2 for measuring bio-signals. Hereinafter, the apparatus 2 and the apparatus 1 are described as separate apparatuses, but one of ordinary skill in the art would understand that the apparatuses 1 and 2 may be realized as one integrated apparatus. In one exemplary embodiment, the apparatus 1 may include a function of measuring a bio-signal.

The apparatus 2 includes a medical apparatus and equipment for measuring a bio-signal of a patient. In one exemplary embodiment, the apparatus 2 may be an electroencephalograph, an apparatus for analyzing brainwaves, a retinal electrometer, a sphygmograph, a tocomonitor, a thermographic device, a slit lamp microscope, an anthropometer, a phonocardiograph, an electrocardiograph, a thermometer, a weighing machine, an ultrasonic blood flow meter, a hemadynamometer, a blood sugar meter, or a spirometer.

In exemplary embodiments, a bio-signal may include, but is not limited to, a brain waves analysis document, an electromyogram, a temperature, a blood pressure level, a weight, a body fat amount, a ratio of alanine transaminase to spartate transaminase ("ALT/AST") and hepatitis B virus deoxyribonucleic acid ("HBV DNA") levels (e.g., liver condition level), cholesterol level, a blood sugar amount, a heart rate, or oxygen saturation. One of ordinary skill in the art would understand that a bio-signal includes all levels, conditions, and symptoms related to health, that the apparatus 2 includes all apparatuses and equipments for determining the bio-signal, and that a plurality of bio-signals may be measured by one singular device.

A patient (FIG. 1) is a person whose bio-signal is measured by using the apparatus 2. The patient may be a person having a health condition that needs to be continuously monitored, but the patient is not limited thereto, and may be any person whose bio-signal is measured. A medical expert (FIG. 1) is generally a doctor or a nurse who monitors and manages a condition of the patient by using the apparatus 2, but is not limited thereto, and may be anyone who uses the apparatus, such as the patient or a caretaker of the patient. The patient and/or the medical expert may be a user of the system for displaying bio-information of the invention.

Referring to FIG. 1, the apparatus 1 includes a monitoring unit 11, a display unit 12, a memory 13, an input unit 14, and a sound emitting unit 15. The apparatus 1 displays (e.g., outputs) information about bio-parameters obtained from the apparatus 2, such as on a screen, monitor or like visual device.

Bio-parameters are numerals or numerical representations indicating a health condition of a patient. Bio-parameters may include, but are not limited to, temperature, heart rate, blood pressure, electrocardiogram ("ECG"), saturation of partial pressure arterial oxygen ("$SpO_2$"), non-invasive blood pressure ("NIBP"), invasive blood pressure ("IBP"), and end tidal carbon dioxide ("$EtCO_2$"). Bio-information includes both of basic information and detailed information about the bio-parameters and/or the patient. The apparatus 1 displays data about the bio-parameters, such as temperature, heart rate, blood pressure, ECG, $SpO_2$, NIBP, IBP, and $EtCO_2$, of the patient on a screen. Basic information of a bio-parameter includes at least one selected from the group consisting of a number and a graph showing measured bio-parameter data. Detailed information of a bio-parameter includes information such as a temporal data tendency of the bio-parameter, in addition to the basic information. Regarding a method of displaying bio-information, bio-information may be displayed on a screen via a visual method, or may be output via an acoustic method, such as emitting a sound via a speaker, or a tactual method.

The monitoring unit 11 monitors the occurrence of an event related to a plurality of bio-parameters. The monitoring unit 11 includes an obtaining unit 111 and an event detecting unit 112. The obtaining unit 111 obtains at least one selected from the group consisting of data about bio-parameters of a patient, an input signal received via the input unit 14, and other information about the bio-parameters.

The data about the bio-parameters obtained by the obtaining unit 111 may be output via the display unit 12 and/and the sound emitting unit 15, or stored in the memory 13. The data about the bio-parameters obtained by the obtaining unit 111 is measured data about ECG, $SpO_2$, NIBP, IBP, or the like of the patient. In one exemplary embodiment, when a bio-parameter is $SpO_2$, data about the bio-parameter is a value of $SpO_2$, such as 88%, measured by the apparatus 2.

A signal received by the obtaining unit 111 via the input unit 14 is a signal corresponding to selection information input by a user of the system for displaying bio-information of the invention. In other words, the obtaining unit 111 obtains information input by the user via the input unit 14, so as to convert information about bio-parameters (e.g., the data about the bio-parameter) displayed on the display unit 12, into other information.

The other information about bio-parameters converted by the obtaining unit 111 includes information required to monitor the occurrence of an event. The event may be set to various cases, such as a case where a condition of a patient deteriorates, a case where the condition improves, where a condition emerges such as an emergency, according to a setting made by the user. In one exemplary embodiment, when the event is set to a case where the condition deteriorates, the obtaining unit 111 obtains normal range data of each bio-parameter. When a bio-parameter is $SpO_2$, and $SpO_2$ may have a value in a range of about 85% to about 100%, the obtaining unit 111 may obtain data that a lower limit threshold value of a normal range of $SpO_2$ is about 85% and an upper limit threshold value of the normal range of $SpO_2$ is about 100%. The obtaining unit 111 may obtain the above data from the user via the input unit 14 and/or may use data stored in the memory 13.

The event detecting unit 112 monitors the occurrence of the event according to a default setting and/or a setting of the user based on the data obtained by the obtaining unit 111. As described above, the event may be various cases, such as an improvement or deterioration in condition, or an emergency condition of a patient.

When the event is an emergency, the obtaining unit 111 obtains data of bio-parameters from the apparatus 2, and obtains a normal range of the bio-parameters. The event detecting unit 112 compares the obtained data from the obtaining unit 111 with the normal range. When the obtained data is not within the normal range, the event detecting unit 112 detects the event, e.g., detects the occurrence of the emergency.

When the event is a case of receiving a screen conversion command from the user, the obtaining unit 111 obtains a signal from the input unit 14, and the event detecting unit 112 detects the event according to the signal of the obtaining unit 111 and converts a screen of the display unit 12.

The emergency and the screen conversion command are just examples of the event, and thus the event is not limited thereto, and may include various conditions, such as an improvement in a health condition, according to a setting of the user.

Figure 2:
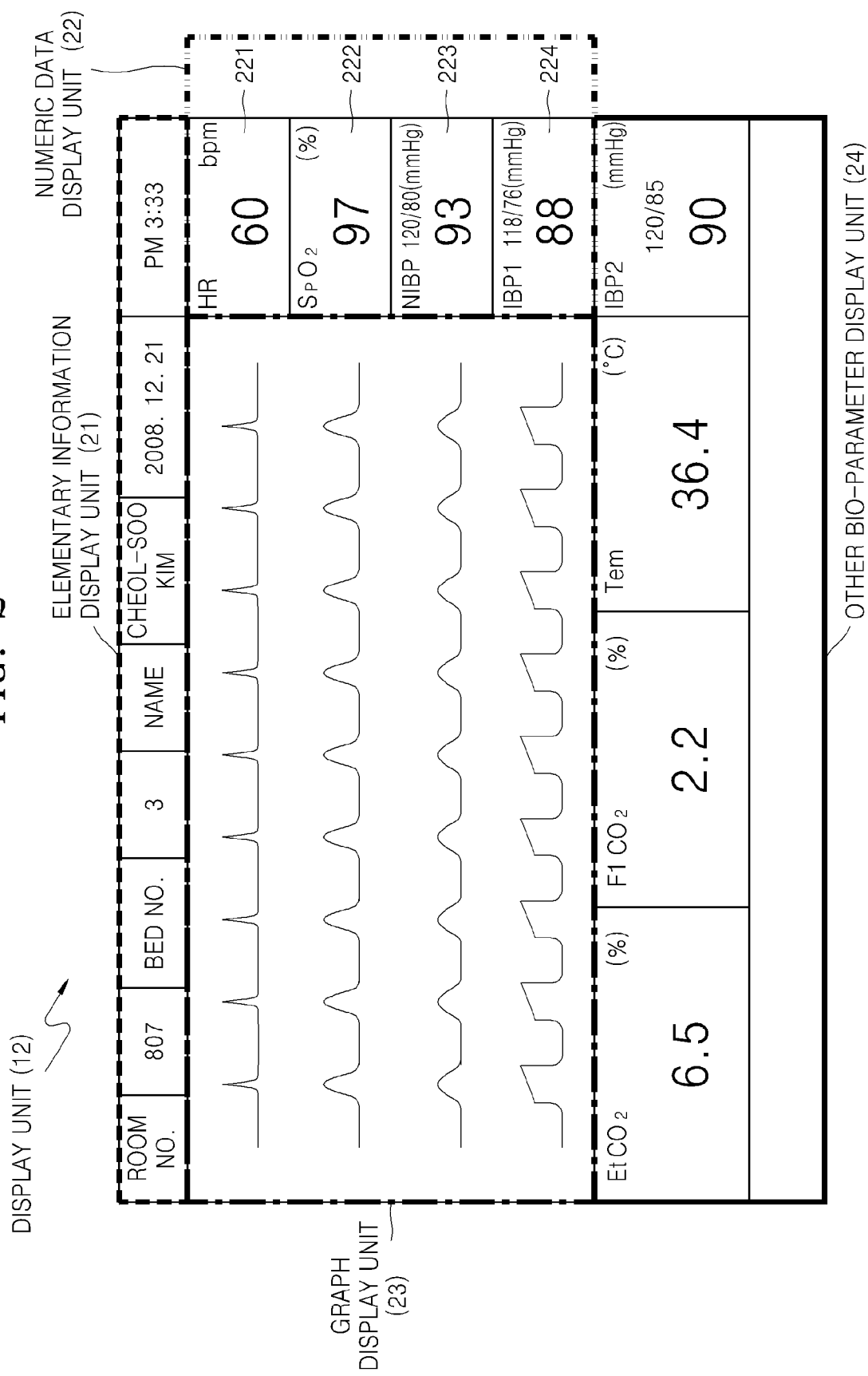
FIG. 2 is a diagram illustrating an exemplary embodiment of a screen displaying basic bio-information of a plurality of bio-parameters.

The display unit 12 displays at least one selected from the group consisting of the basic bio-information and the detailed bio-information about the bio-parameters obtained by the monitoring unit 11. FIG. 2 is a diagram illustrating an exemplary embodiment of a screen displaying basic bio-information of a plurality of bio-parameters.

Referring to FIG. 2, the display unit 12 includes an elementary information display unit 21, a numeric data display unit 22, a graph display unit 23 and an other bio-parameter display unit 24. The elementary information display unit 21 displays at least one selected from the group consisting of the basic information of a patient, and/or information about a current date and time.

The numeric data display unit 22 displays data about bio-parameters as numbers.

The graph display unit 23 displays the data about bio-parameters in a graph form. The graph display unit 23 in FIG. 2 includes the area showing four horizontally extending graphs.

The other bio-parameter display unit 24 displays data about bio-parameter other than those displayed by the numeric data display unit 22. The other bio-parameter display unit 24 in FIG. 2 includes the data at the bottom of the display unit 12, extending from the "$E_tCO_2$" at the left, to the "IBP2 (mmHg)" at the right.

One of ordinary skill in the art would understand that FIG. 2 is only an exemplary embodiment of displaying a plurality of pieces of bio-information on one single view screen, that a configuration and method of displaying bio-information is not limited thereto, and that bio-information may be displayed via any of a number of configurations and/or methods, having a similar function as that of FIG. 2.

A graph in the graph display unit 23 displays data about bio-parameters measured by the apparatus 2, according to time. The numeric data display unit 22 shows values, which are measured by the apparatus 2, as numbers.

The elementary information display unit 21 displays at least one selected from the group consisting of identification information about a patient, and/or information about an environment at which the patient is located, such a current date and time of operating the apparatus 1. As described above, the patient is a person whose bio-signals are measured by using the apparatus 2. The elementary information display unit 21 shows a person to whom the bio-parameters displayed on the display unit 12 belong. In one exemplary embodiment, when the apparatus 1 is used in a hospital, FIG. 2 shows that the elementary information display unit 21 of the display unit 12 displays bio-information of the patient named "Cheol-soo Kim" in "Bed No. 3" in "Room No. 807." Also, FIG. 2 shows that the bio-information is measured at "3:33" pm on "21 Dec. 2008."

The numeric data display unit 22 displays numeric data of the bio-parameters obtained from the monitoring unit 11. When a plurality of bio-signals are measured by the apparatus 2, data of each of a plurality of bio-parameters are displayed with a label or name of the corresponding bio-parameter. In the illustrated embodiment, bio-signals measured by the apparatus 2 may be heart rate ("HR"), $SpO_2$, NIBP, IBP1, IBP2, and/or temperature. Measured values of the plurality of bio-parameters are displayed on the numeric data display unit 22.

Referring to FIG. 2, the numeric data display unit 22 includes an HR display area 221, a $SpO_2$ display area 222, an NIBP display area 223, and an IBP 1 display area 224. Referring to the numeric data display unit 22 in FIG. 2, HR is 60 beats per minute ("bpm"), $SpO_2$ is 97%, diastolic pressure is 120 millimeters of mercury ("mmHg"), systolic pressure is 80 mmHg, and mean blood pressure is 93 mmHg in NIBP, and diastolic pressure is 118 mmHg, systolic pressure is 76 mmHg, and mean blood pressure is 88 mmHg in IBP1.

The graph display unit 23 displays graph data of bio-parameters obtained from the monitoring unit 11. When a plurality of bio-signals are measured by the apparatus 2, the graph display unit 23 the measured bio-signal data by outputting a name or other identification of a corresponding bio-parameter. The graph display unit 23 and the numeric data display unit 22 generally operate as a pair. In other words, when the numeric data display unit 22 includes the HR display area 221, the $SpO_2$ display area 222, the NIBP display area 223, and the IBP 1 display area 224, the graph display unit 23 also displays a time-series graph based on the above bio-parameters.

In an exemplary embodiment, each graph of the graph display unit 23 may be classified by using at least one method selected from the group consisting of a method of outputting a name of a corresponding bio-parameter relative to each graph, a method of matching a color of a number output on the numeric data display unit 22 and a color of a corresponding graph in the graph display unit 23, and/or a method of locating a graph on a left side of the numeric data display unit 22 such that the display areas 221 through 224 are aligned with the actual graph within the graph display unit 23.

The other bio-parameter display unit 24 obtains measured data from the apparatus 2, and simply displays numeric data without a graph, according to a setting of a user or a default setting of the apparatus 1. When a plurality of bio-parameters are displayed on the other bio-parameter display unit 24, readability of view of the display unit 12 may remarkably deteriorate if too much information is displayed on graphs and as numeric data at once. An alternative embodiment of the display unit 12 includes a whole or a portion of the other bio-parameter display unit 24 being omitted.

One of ordinary skill in the art would understand that FIG. 2 is only an exemplary embodiment of displaying bio-information related to a plurality of bio-parameters, and that the bio-information about the bio-parameters may be displayed by using other methods. Also, the number of bio-parameters of which the bio-information is displayed on one screen may be limited to two or three according to a setting of a medical expert or the user, and moreover, the medical expert may select bio-information to be displayed on one viewing screen.

Referring to FIG. 1, the display unit 12 displays basic bio-information about more than one of the bio-parameters on a first screen, and when the monitoring unit 11 detects an event, the display unit 12 converts the first screen from displaying the basic bio-information, to a second screen displaying detailed bio-information of at least one of the plurality of bio-parameters. When the detected event is an emergency, detailed bio-information about a bio-parameter related to the emergency is displayed on the display unit 12. When the event is an input of a screen conversion command from a user, such as a medical expert, the monitoring unit 11 detects the event according to a signal obtained from the input unit 14, and the display unit 12 displays detailed bio-information in the second screen about a bio-parameter according to an order of the screen conversion command.

Figure 3:
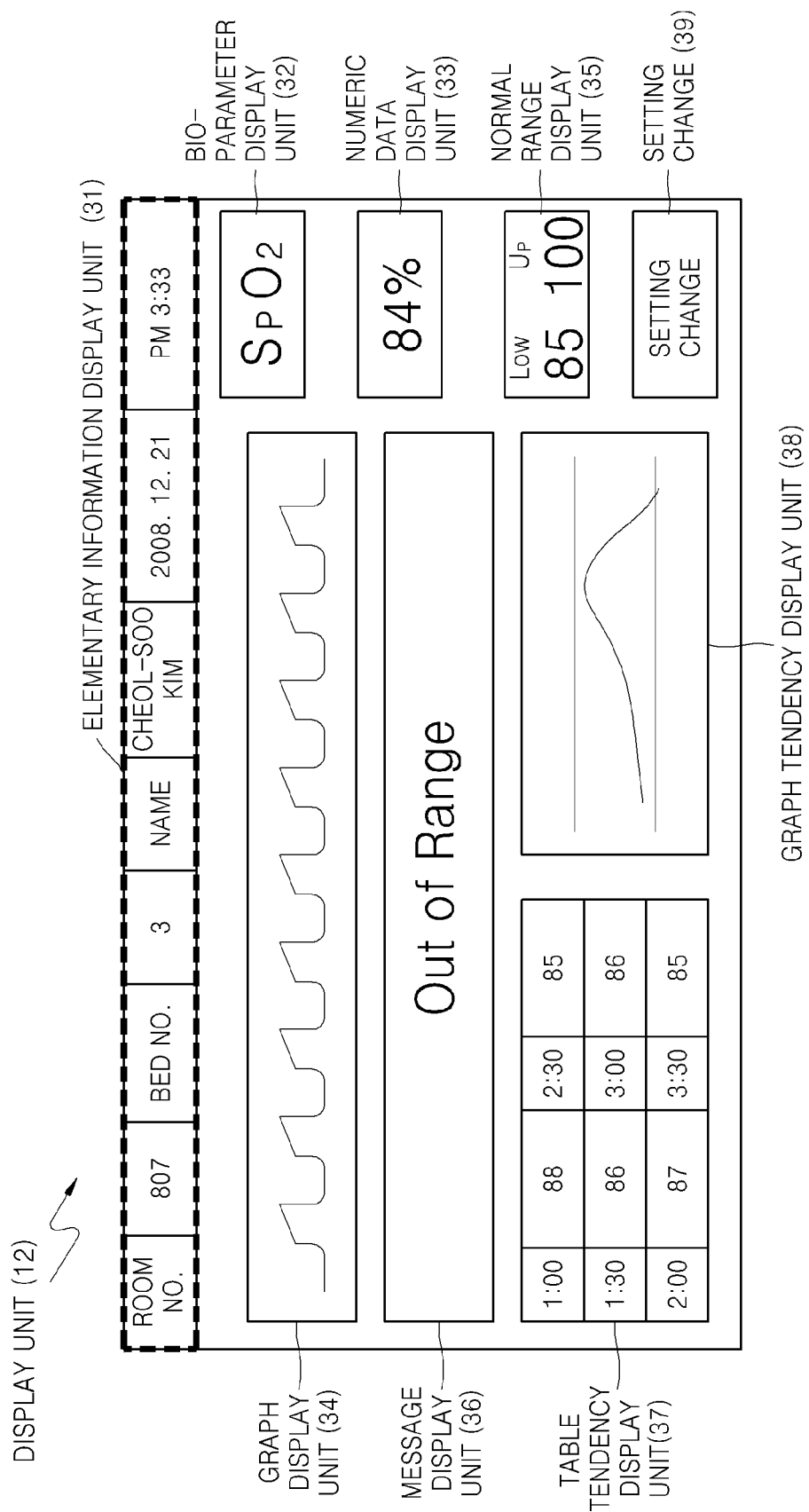
FIG. 3 is a diagram illustrating an exemplary embodiment of a screen displaying bio-information of only a blood oxygen saturation bio-parameter.

In one exemplary embodiment, when the event is an emergency and the event is detected based on $SpO_2$ not being within a normal range, the display unit 12, which was displaying a plurality of pieces of bio-information for the more than one bio-parameter in the first screen, is converted to only display detailed bio-information of $SpO_2$ in the second screen. FIG. 3 is a diagram illustrating an exemplary embodiment of a second screen displaying bio-information related to only $SpO_2$.

Referring to FIG. 3, the display unit 12 of the converted second screen includes an elementary information display unit 31, which displays at least one selected from the group consisting of basic information of a patient and information about a current date and time, a bio-parameter display unit 32, which shows which bio-parameter is being displayed on the converted second screen, a numeric data display unit 33, which displays the bio-parameter as a numeral, a graph display unit 34, which displays the bio-parameter in a graph, a normal range display unit 35, which displays a lower limit value and an upper limit value of a normal range of the bio-parameter, a message display unit 36, which displays a textual or alphanumeric message to notify a user or observer of the display unit 12 about a condition of a patient, a table tendency display unit 37, which displays a tendency of the bio-parameter according to time in a table, a graph tendency display unit 38, which displays a tendency of the bio-parameter according to time in a graph, and a setting change 39 about a screen setting. One of ordinary skill in the art would understand that FIG. 3 is only an exemplary embodiment of displaying detailed bio-information of one bio-parameter on one screen, and that the detailed bio-information related to the one bio-parameter may be displayed by using other methods.

The detailed bio-information displayed on the converted second screen further includes at least one selected from the group consisting of the table tendency display unit 37 and the graph tendency display unit 38, which show a data tendency according to time, in addition to the basic bio-information. The data tendency denotes statistical data according to the time, wherein the data was measured by the apparatus 2. In other words, the data tendency denotes data changing of the bio-parameter in units of time, where the data is illustrated in at least one selected from the group consisting of a table and a graph, so that a change in data is perceived at a glance.

In detail, referring to FIG. 3, the bio-parameter display unit 32 shows for which bio-parameter the basic and/or detailed bio-information is displayed on the converted second screen. Types of a bio-parameter include $SpO_2$, temperature, HR, and blood pressure. The bio-parameter display unit 32 may display names of the above types. In FIG. 3, a bio-parameter represented by the display on the display unit 12 is $SpO_2$.

The elementary information display unit 31, the numeric data display unit 33, and the graph display unit 34 respectively correspond to the elementary information display unit 21, the numeric data display unit 22, and the graph display unit 23 of FIG. 2. However in FIG. 3, the numeric data display unit 33 and the graph display unit 34 output data about only one bio-parameter. In other words, referring to FIG. 3, a value of "$SpO_2$," of the patient named "Cheol-soo Kim" in "Bed No. 3" in "Room No. 807" is "84%" at "3:33 pm" on "21 Dec. 2008".

The normal range display unit 35 of the converted second screen displays a normal range of the bio-parameter obtained from a medical expert, and/or a normal range of a bio-parameter stored in the apparatus 1 as a default setting. As described above, the medical expert is a person who monitors and analyzes bio-information of a person to be measured, e.g., a patient, by using the apparatus 1. In an exemplary embodiment, when the apparatus 1 is used in a hospital, the medical expert is a doctor or a nurse. In other words, the medical expert may set (e.g., manually) normal ranges of bio-parameters. Alternatively, when the medical expert does not set the normal ranges, stored values are generally set as the normal ranges.

In an exemplary embodiment illustrated in FIG. 3, when the bio-parameter displayed on the display unit 12 of the apparatus 1 is $SpO_2$, a normal range of $SpO_2$ is generally in a range of about 85% to about 100%. Accordingly, the normal range display unit 35 displays at least one selected from the group consisting of a lower limit value and an upper limit value of the normal range of the bio-parameter.

The message display unit 36 displays a message about a condition of a patient. When the monitoring unit 11 obtains a data value for a bio-parameter, the monitoring unit 11 compares the value of the obtained bio-parameter with the set normal range. When the value of the bio-parameter is within the normal range, the message unit 36 may display a phrase such as "Normal," and when the value of the bio-parameter is not within the normal range, the message unit 36 may display a phrase such as "Emergency."

In an exemplary embodiment, when the normal range of $SpO_2$ about 85% to about 100%, the message display unit 36 displays a message meaning that a condition of the patient is fine, such as "Normal," if the $SpO_2$ is 90%. Alternatively, according to a setting of the apparatus 1, the message display unit 36 may be left empty when the condition of the patient is fine, and a message will display only when a measured value of a bio-parameter is out of the normal range (e.g., the patient is not fine).

Conversely, when the data value for $SpO_2$ is 84%, the $SpO_2$ is not within the normal range about 85% to about 100%, and thus the message display unit 36 may display a message indicating that the condition of the patient is in an emergency, such as "Emergency," "Outside Range" or "$SpO_2$ Failure."

When an emergency occurs, the sound emitting unit 15 may emit an alarm. The sound emitting unit 15 may sound an audible alarm to alert the medical expert and notify the medical expert that the condition of the patient is outside the normal range. In an exemplary embodiment, the alarm may be emitted by using a method of emitting an audible sound via a speaker, and the emitted audible sound may be an electric sound, a voice, or the like.

The table tendency display unit 37 or the graph tendency display unit 38 displays a changing amount (e.g., a history) of a bio-parameter according to time, respectively in a table or a graph. Referring to FIG. 3, data values changing according to time, such as $SpO_2$ being 88% at 1:00 pm, and 86% at 1:30 pm, is shown in a table and/or a graph, so that a medical expert may determine a changing state of a bio-parameter of a patient at a glance. In response to the displayed history, the medical expert may change a setting value of the table or the graph. In one exemplary embodiment, values of the bio-parameter in the converted second screen may be shown in a table and/or a graph for a time interval of 10 minutes, 30 minutes, or 1 hour.

The setting change 39 is an input signal obtained for changing a screen configuration of the display unit 12, changing an upper and lower limit value of a normal range, and/or changing the bio-parameter represented by the display of the converted second screen. The setting change 39 is an example of the input unit 14, and an input signal may be input to the apparatus 1 as a medical expert touches a physical area of the display unit 12 where the setting change 39 is shown, or presses an input button separate from physical display unit 12 connected to the setting change 39.

One of ordinary skill in the art would understand that the converted second screen illustrated in FIG. 3 is an exemplary embodiment, and that only required information (e.g., a subset of the information shown in FIG. 2) may be selected and displayed on the screen, or other information related to the bio-parameter may be further displayed on the screen in addition to the information shown in FIG. 2.

When the event is an acquisition of a screen conversion command from a user, selection information of the user is received from the input unit 14, the monitoring unit 11 detects the event, and the first the display unit 12 is converted to a second screen which displays detailed bio-information of one bio-parameter, while displaying a plurality of pieces of bio-information.

A conversion order is based on a default setting, but may be changed by the user. When the user, e.g., a medical expert, inputs the selection information via an input device, the monitoring unit 11 obtains an input signal via the input unit 14, and the display unit 12 converts displayed first screen bio-information according to the input signal corresponding to an event from the monitoring unit 11. Bio-parameters obtained from the apparatus 2 are arranged according to a conversion order, e.g., an order set by the user or an order determined in a default setting, and a bio-parameter having the highest priority is initially displayed via the display unit 12.

Figure 4:
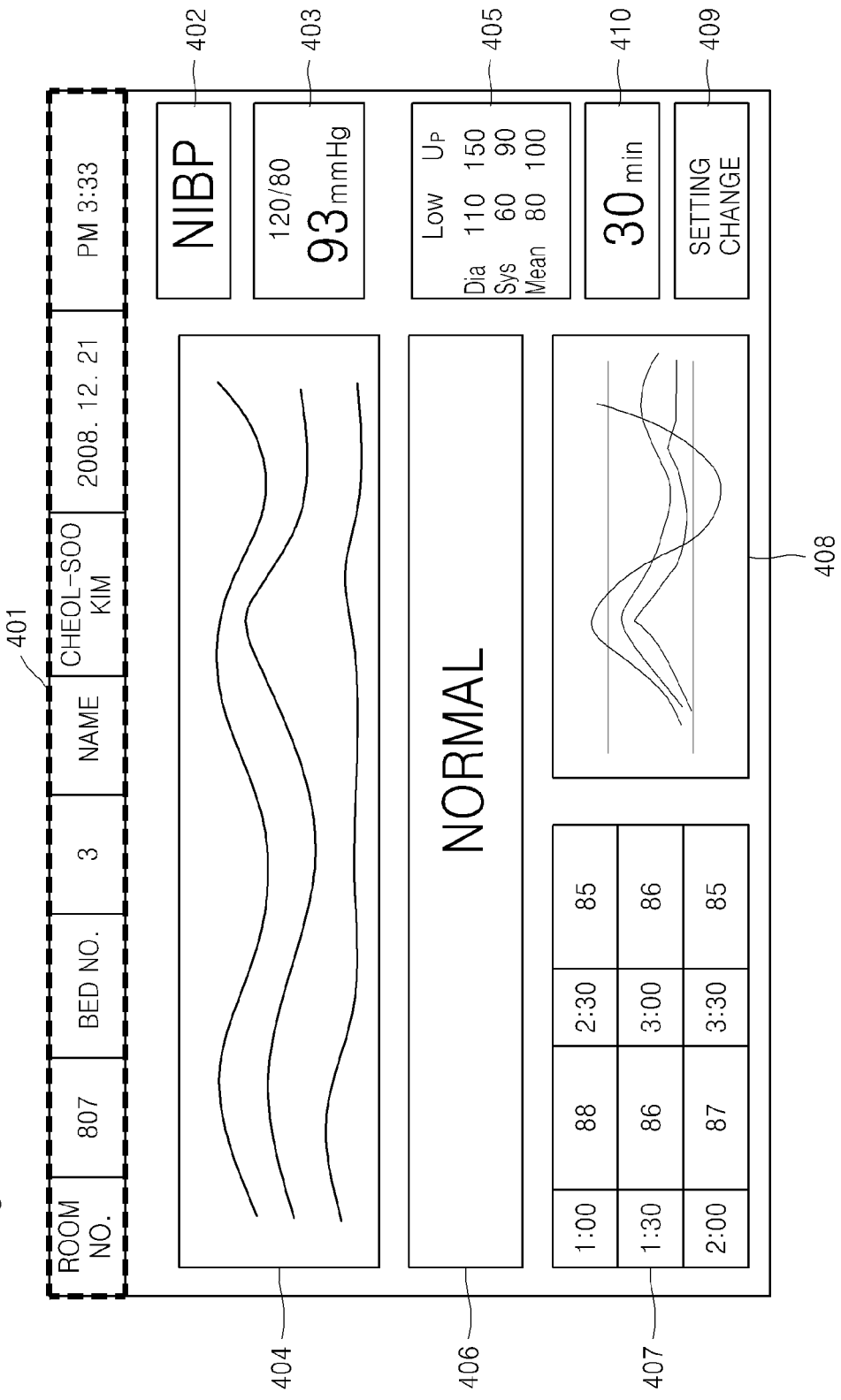
FIG. 4 is a diagram illustrating an exemplary embodiment of a screen displaying bio-information of only a non-invasive blood pressure bio-parameter.

Assuming that detailed information of NIBP is displayed on the second screen according to the screen conversion command, FIG. 4 is a diagram illustrating an exemplary embodiment of a converted second screen displaying bio-information from only NIBP. A screen configuration of FIG. 4 may be identical to that of FIG. 3, or a measurement interval display unit 410 may be further included in the screen configuration of FIG. 3.

Referring to FIG. 4, a bio-parameter display unit 402 displays NIBP. Numeric data, graph data, and a normal range of NIBP are respectively displayed on an elementary information display unit 401, a numeric data display unit 403, a graph data display unit 404, a normal range display unit 405 and a message display unit 406. Also, a data tendency is displayed on a table and a graph, respectively on a table tendency display unit 407 and a graph tendency display unit 408. Also, the display unit 12 of FIG. 4 includes a setting change 409 for changing a setting.

The display unit 12 may display bio-information related to the bio-parameter of a patient on the screen according to the measurement interval display unit 410. In an exemplary embodiment, the bio-parameter may be measured during a time interval of the measurement interval display unit 410 set by a medical expert, or may store a data tendency for a thirty minute interval of the measurement interval display unit 410, in the memory 13. Referring to FIG. 4, values of the NIBP are stored for a 30 minute time interval, and the stored values are shown in a table and/or a graph on the display unit 12.

By outputting the bio-information for only one bio-parameter on one screen, readability by a medical expert of the bio-parameter of a patient increases. Bio-information for a plurality of bio-parameters may be displayed on one screen, and alternatively, only bio-information for a required bio-parameter may be displayed on the one screen so as to efficiently monitor and analyze the required bio-parameter, such as when the required bio-parameter needs to be intensively monitored and analyzed.

Referring back to FIG. 1, the memory 13 stores bio-parameters, an algorithm for controlling the apparatus 1, and other information. The memory 13 stores a normal range of each bio-parameter described above, user information, etc. Also, in order to display a data tendency according to time in a table or a graph, the memory 13 may store bio-parameters according to each time, and display a bio-parameter if required.

The input unit 14 receives selection information from a medical expert, a patient or other user. The monitoring unit 11 arranges a plurality of bio-parameters obtained from the apparatus 2 according to a conversion order, e.g., an order set by a user of the apparatus 1 or an order determined in a default setting, and when a signal is received from the input unit 14, the display unit 12 converts a first screen into a second screen according to the conversion order.

The input unit 14 receives selection information from a user being at least one selected from the group consisting of a patient and a medical expert. The input unit 14 operates the apparatus 1 according to a purpose of the user, and obtains a signal via an input device, such as a touch screen, keyboard, a mouse, a button, or a voice recognizer.

In one embodiment as an illustration of the invention, the apparatus 2 measured HR, $SpO_2$, NIBP, and IBP. The apparatus 1 obtained the measured data for HR, the $SpO_2$, the NIBP, and the IBP. A priority of bio-parameters may be determined according to a default setting of the apparatus 1, or determined by a medical expert. In the illustrated embodiment, the priority order may be the HR, the $SpO_2$, the NIBP, and the IBP.

When the display unit 12 initially displays the HR and receives a signal from the medical expert, for example, receives selection information input by pressing an input button or by using a keyboard, the display unit 12 subsequently displays the $SpO_2$, which is in a priority order after the HR. Information of the first screen displayed on the display unit 12 is converted to the second screen according to the priority order, whenever the conversion signal from the medical expert is received. Since screen conversion rotates, when the display unit 12 displays information having the lowest priority and the conversion signal is received, the display unit 12 again displays information having the highest priority, e.g., the HR. In an exemplary embodiment, after a lower priority bio-parameter is displayed on the converted second screen, the medical expert may go back to a higher priority bio-parameter or may continue only to a lower priority bio-parameter up to the lowest priority bio-parameter.

When there are a plurality of bio-parameters, only bio-information for one bio-parameter is displayed on the one converted second screen so as to increase readability of a medical expert, and the plurality of bio-parameters may be easily monitored and analyzed with simple manipulation based on the priority order of the bio-parameters. When the medical expert is searching for a bio-parameter to be monitored, the medical expert may operate the apparatus 1 that outputs the bio-information for the bio-parameter with simple manipulation, such as by pressing a button on the display unit 12 and/or interfaced with the apparatus 1 to affect the manipulation.

When an event is detected by the monitoring unit 11, the sound emitting unit 15 emits an audible sound notifying a user or an observer of the occurrence of the event. The sound emitting unit 15 is generally a speaker, but is not limited thereto, and may be any device outputting an audible sound.

Elements of the apparatus 1 described above, may correspond to one or more processors of the apparatus 1, such as a computer processor. A processor may be realized in an array of a plurality of logic gates, or in combination of a general-use microprocessor and a memory storing a program to be executed in the general-use microprocessor. Alternatively, the processor may be realized in hardware having another structure. One of ordinary skill in the art would understand that the apparatus 1 may further include a controller (not shown) for controlling the elements of the apparatus 1.

FIG. 5 is a flowchart illustrating an exemplary embodiment of a method of converting a first bio-information display screen to a second bio-information display screen when an emergency occurs. The method includes operations that are performed sequentially in the apparatus of FIG. 1. Accordingly, the details or features described above with reference to the apparatus of FIG. 1, may be applied as details that are omitted while describing the method.

In operation 501, the apparatus 1 obtains data of bio-parameters from the apparatus 2 which measures bio-signals.

In operation 502, the bio-information of a patient is displayed on the display unit 12. The bio-information may be displayed on a screen by using a visual method, or the bio-information may be emitted as a sound via a speaker by using an acoustic method. For convenience of description, it is assumed that the bio-information is displayed on a screen. Bio-information for a plurality of bio-parameters may be displayed on one screen, or bio-information for one bio-parameter may be displayed on one screen.

In operation 503, the monitoring unit 11 compares each of the obtained data for a plurality of bio-parameters with a normal range for the bio-parameters. In an exemplary embodiment, the monitoring unit 11 compares the measured data value of a bio-parameter with pre-set upper and lower limit values of a normal range of the bio-parameter.

According to the result of the comparing, the monitoring unit 11 detects an event by determining whether a bio-parameter that is not within the normal range exists. If it is determined that a bio-parameter that is not within the normal range exists, e.g., when there is a bio-parameter in an emergency condition, operation 504 is performed. Conversely, if it is determined that all bio-parameters are within the normal ranges, operation 502 is performed.

When an emergency occurs, the monitoring unit 11 determines a number of bio-parameters in an emergency condition in operation 504. In an exemplary embodiment, when the number of the bio-parameters in an emergency condition is only one, operation 505 is performed, and when the number of bio-parameters in an emergency condition is two or more, operation 506 is performed.

In operation 505, after it has been determined that the number of the bio-parameters in an emergency condition is only one, detailed bio-information of the one bio-parameter in the emergency condition is displayed on the screen of the display unit 12, and at least one operation selected from the group consisting of a warning message displaying operation and an alarm generating operation is performed.

In operation 506, when it has been determined that the number of bio-parameters in an emergency condition is two or more, the display unit 12 alternatively displays the bio-information of the two or more bio-parameters in an emergency condition according to a priority and a time interval. In an exemplary embodiment, detailed bio-information of any one of the two or more bio-parameters in an emergency condition is displayed on the screen of the display unit 12, at least one operation selected from the group consisting of a warning message displaying operation and an alarm generating operation is performed for the any one of the two or more bio-parameters, and the same operation is performed on another of the two of more bio-parameter in an emergency condition during a time interval.

Figure 6A:
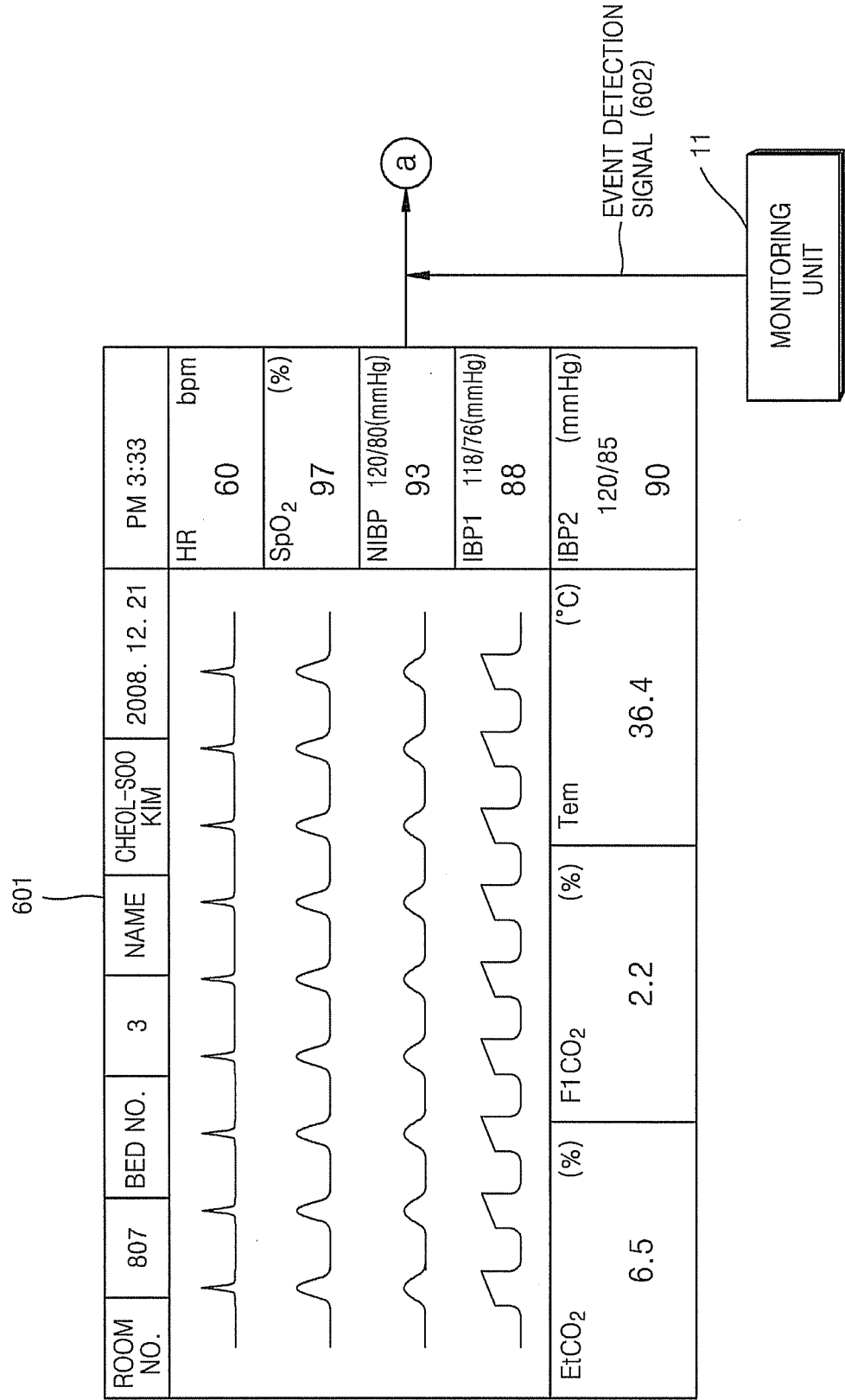
Figure 6B:
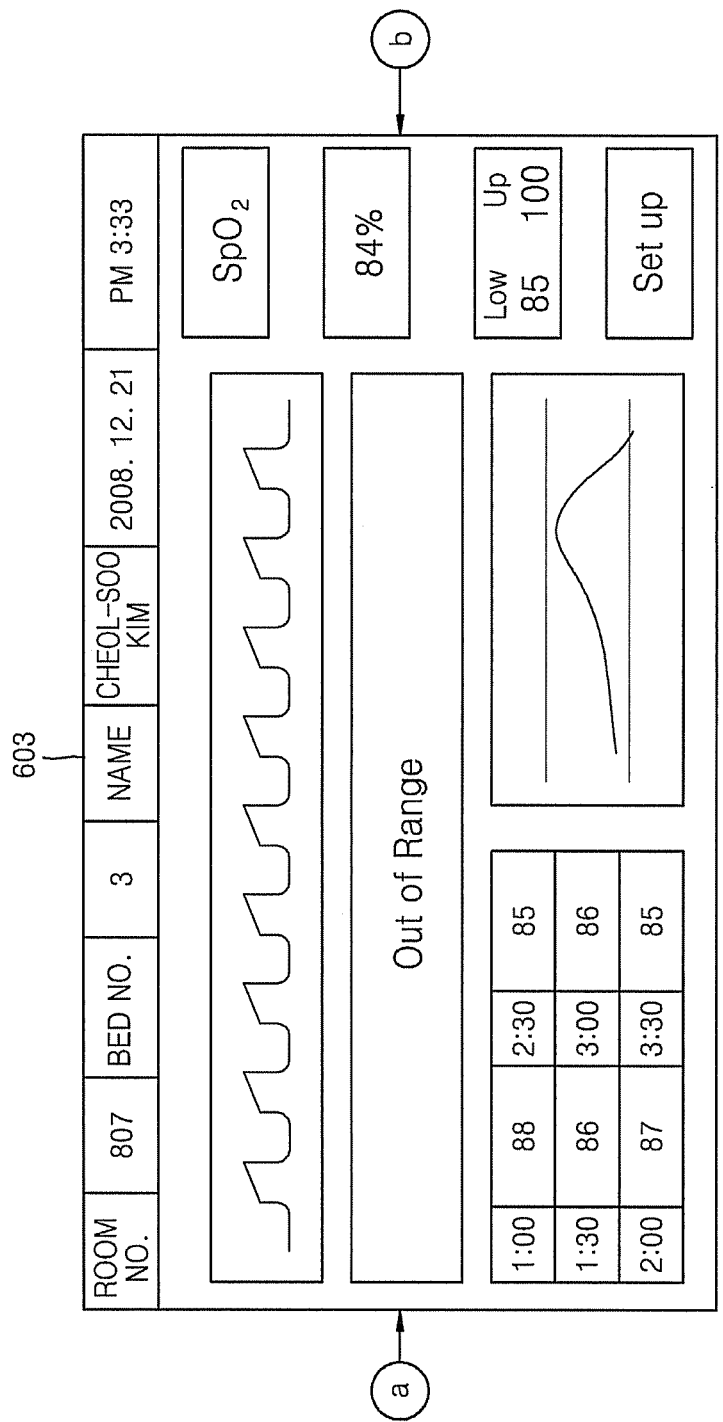

FIGS. 6A-C are diagrams for describing an exemplary embodiment of a bio-information display screen conversion of the display unit 12. For convenience of description, when it is assumed that the display unit 12 is a screen for displaying bio-information relative to a bio-parameter, the display unit 12 displays bio-information obtained from the apparatus 2 as shown in a first screen 601. Here, basic information of a plurality of pieces of bio-information may be displayed, or detailed information of one piece of bio-information may be displayed.

While basic information of a plurality of pieces of the bio-information is displayed on the first screen 601, the display unit 12 displays detailed information of one piece of the plurality of pieces of the bio-information according to an event detection signal 602 from the monitoring unit 11, as shown in a second screen 603. As described above, the event detection signal 602 is a signal triggering the display of detailed information of the one piece of bio-information on a second screen, when the one bio-information satisfies a condition, such as the occurrence of an emergency or condition improvement.

When the number of pieces of bio-information satisfying the condition is two or more, the two or more pieces of bio-information are alternatively displayed according to the priority during a time interval. In one exemplary embodiment, when the bio-parameters $SpO_2$ and NIBP are outside a normal range and thus an emergency occurs, the display unit 12 displays detailed information of the bio-parameter $SpO_2$ as shown in the second screen 603, and then displays detailed information of the bio-parameter NIBP as shown in a third screen 605, after a time interval 604. When the time interval 604 is three seconds, the bio-information related to the $SpO_2$ and the NIBP are both displayed on the display unit 12 during a time interval of three seconds.

Figure 7A:
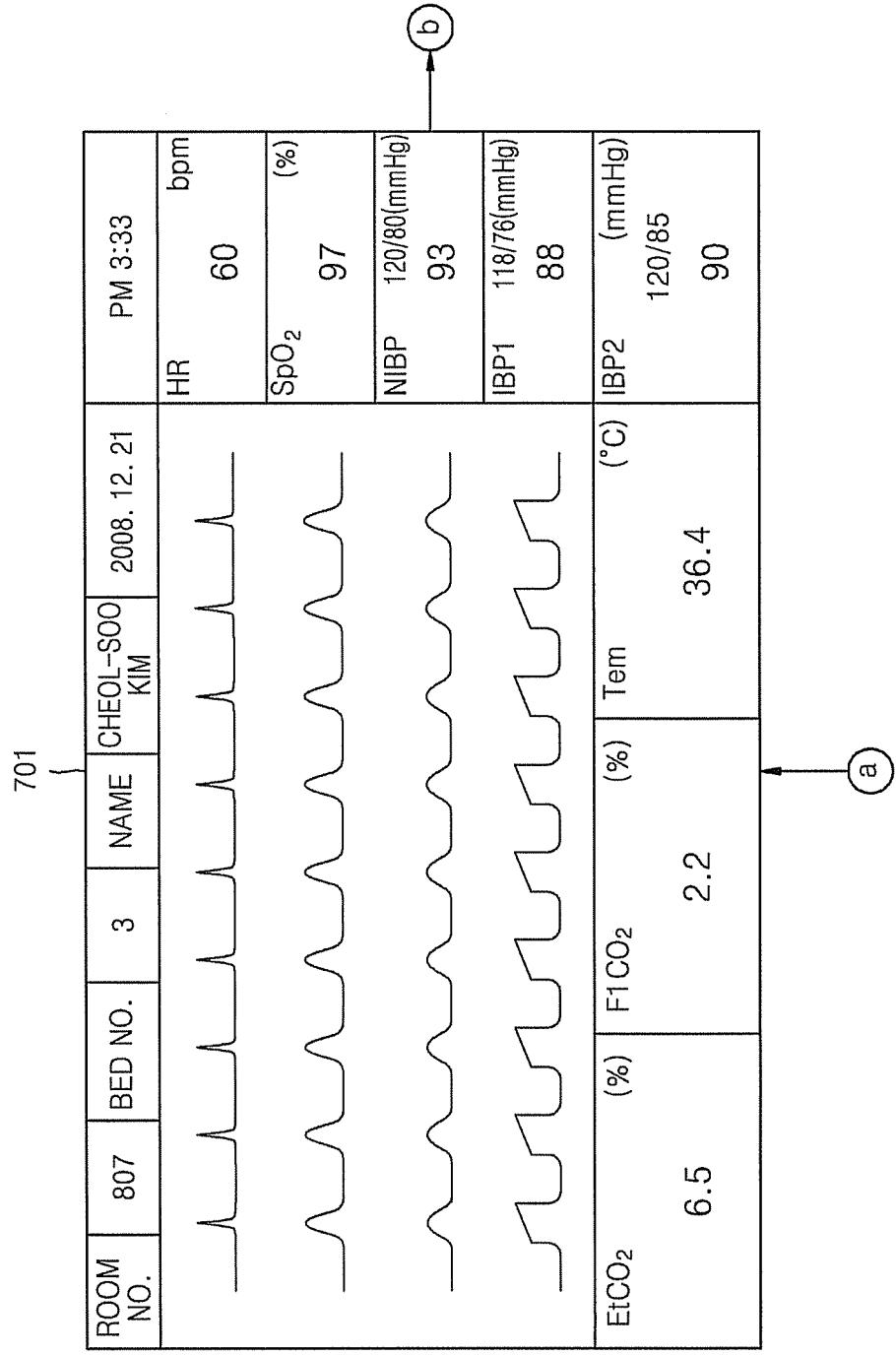
FIGS. 7A-C are diagrams for describing an exemplary embodiment of a bio-information display screen conversion of a display unit, when selection information of a user is received.
Figure 7B:
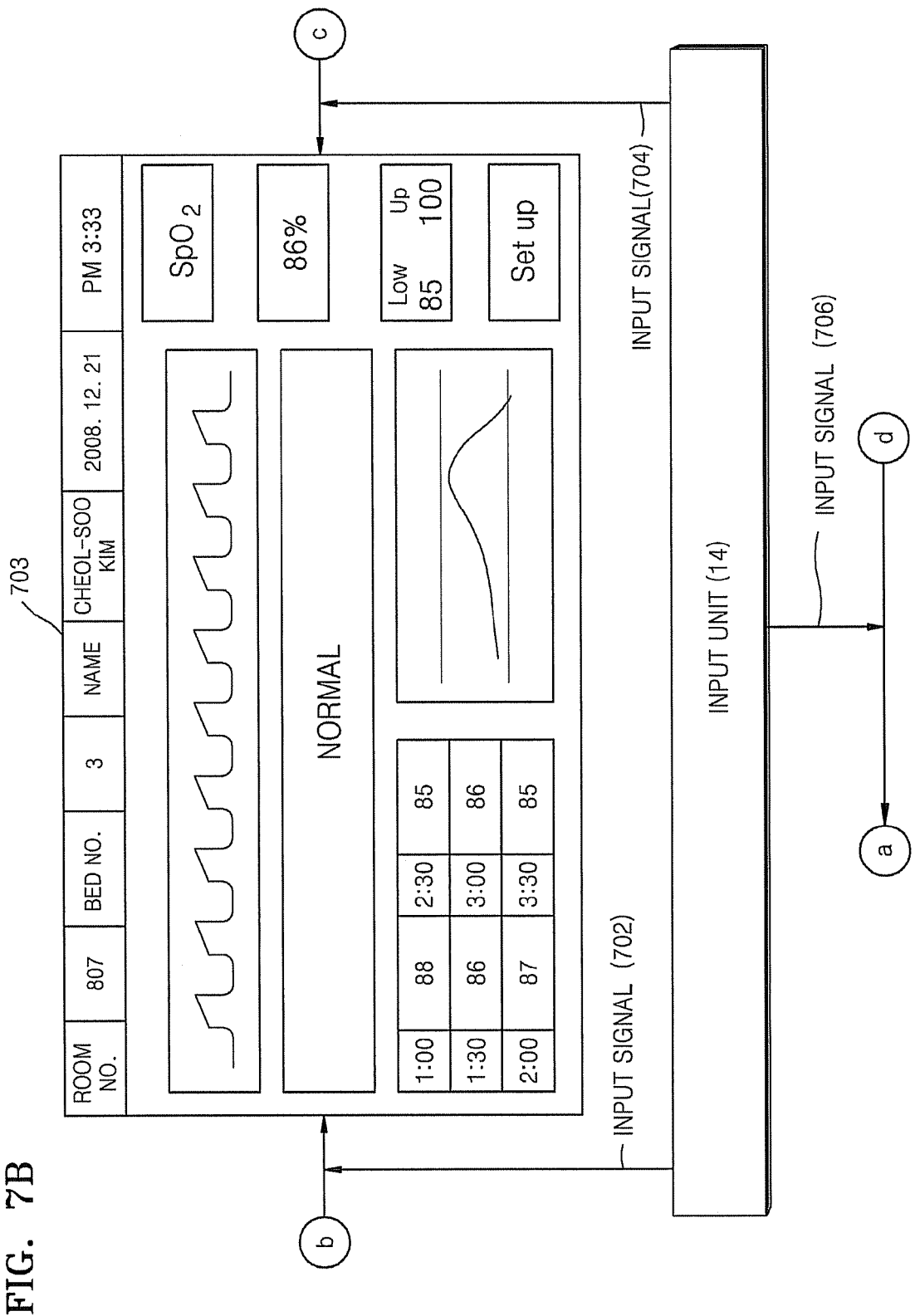
Figure 7C:
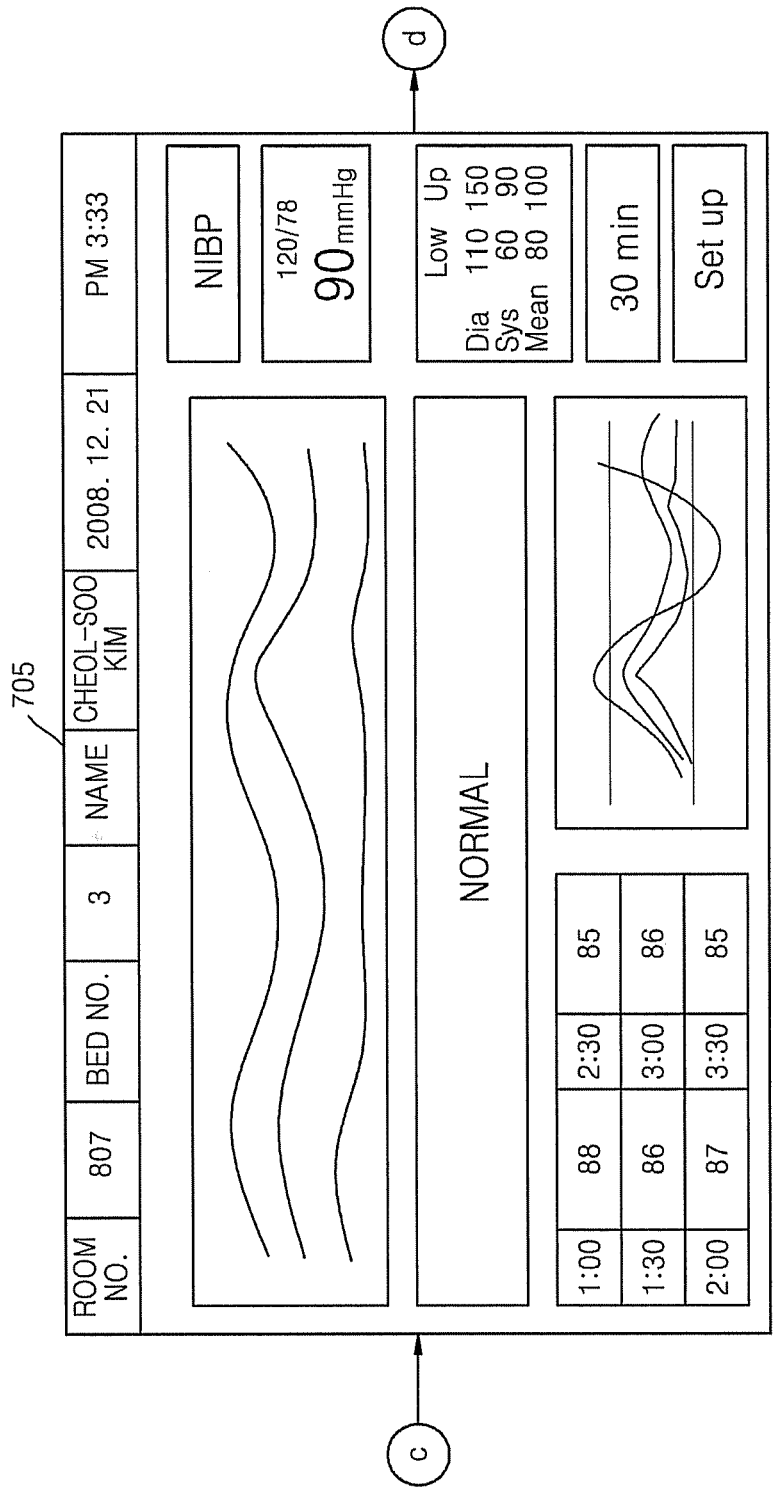

FIGS. 7A-C are diagrams for describing an exemplary embodiment of a bio-information display screen conversion of the display unit 12, when selection information of a user is received. For convenience of description, when it is assumed that the display unit 12 is a screen for displaying bio-information relative to a bio-parameter, the display unit 12 displays bio-information obtained from the apparatus 2, as shown in a first screen 701. Here, basic information of a plurality of pieces of bio-information may be displayed, or detailed information of one piece of bio-information may be displayed.

While basic information of a plurality of pieces of the bio-information is displayed on the first screen 701, when at least one selected from the group consisting of a patient and a medical expert inputs a first input signal 702 of selection information via the input unit 14, the display unit 12 displays detailed information of one the plurality of pieces of the bio-information according to the first input signal 702 as shown in a second screen 703.

As described above, the first input signal 702 is a signal corresponding to information input via an input device, such as a keyboard, a mouse, or an input button, by at least one selected from the group consisting of the patient and the medical expert. Bio-information for a bio-parameter is displayed on a screen of the display unit 12 according to a priority order, and such a priority order is determined by a default setting or by at least one selected from the group consisting of the patient and the medical expert.

While the display unit 12 displays detailed information of the one the plurality of pieces of the bio-information in the second screen 703, when at least one selected from the group consisting of the patient and the medical expert inputs a second input signal 704 of selection information via the input unit 14, detailed information of one of the plurality of pieces of the bio-information of a next priority order is displayed as shown in a third screen 705. Since the priority order of bio-information rotates, when all bio-information of the plurality of pieces of the bio-information are displayed, and a third input signal 706 is input, the display unit 12 displays the bio-information having the highest priority that was displayed first. In one exemplary embodiment, when the number of bio-information is two, the two bio-information are displayed on one screen, and then individual basic information of the plurality of bio-information, which was initially displayed, is displayed in detail according to a following input signal.

According to the exemplary embodiments, when an emergency occurs, a first screen is immediately converted to a second screen displaying bio-information in the emergency condition, and thus a medical expert is able to quickly determine the emergency. Also, since one piece of bio-information is displayed on the second screen, sizes of a graph, characters, and numerals are visually bigger than then first screen, and thus readability of the medical expert increases.

Also, by converting the screen to only display basic and detailed bio-information for one specific bio-parameter that needs to be attentively observed according to symptoms or condition of a patient, only bio-information required for a disease of the patient may be intensely managed. In one exemplary embodiment, only ECG information may be displayed for a patient with a circulatory organ disease, and only $EtCO_2$ information may be displayed for a patient with a respiratory organ disease. Various pieces of information, such as a data tendency, of one piece of bio-information may be displayed on one screen, and a screen may be converted to display other pieces of bio-information via a simple input method.

As described above, according to the one or more of the above exemplary embodiments, bio-information may be displayed so to be easily understood, a plurality of bio-parameters may be easily controlled, and a condition of a patient and a bio-parameter indicating a problem are easily determined when an emergency occurs. Accordingly, bio-information of the patient may be efficiently monitored.

The examples may be written as computer programs and may be implemented in general-use digital computer processors that execute the programs using a computer readable recording medium. The computer readable recording medium includes, but is not limited to, storage media such as magnetic storage media (e.g., read-only memory ("ROM"), floppy disks, hard disks, etc.), and optical recording media (e.g., compact disc read-only memory ("CD-ROMs") or digital versatile disc/digital video disc ("DVDs")).

It should be understood that the exemplary embodiments described herein should be considered in a descriptive sense only and not for purposes of limitation. Descriptions of features of the invention within each exemplary embodiment should typically be considered as available for other similar features in other exemplary embodiments.

What is claimed is:

1. A method of displaying bio-information, the method comprising:

obtaining basic bio-information of bio-parameters indicating a condition of a patient;

displaying a first screen display including the obtained basic bio-information of the bio-parameters, on a display screen;

comparing, by a processor, a predetermined range of the respective bio-parameters with values corresponding to the obtained basic bio-information of the respective bio-parameters;

determining by a processor, for each of the respective bio-parameters, whether a plurality of events occurs based on whether the values corresponding to the obtained basic bio-information are respectively within the predetermined ranges of the respective bio-parameters; and when the plurality of events occurs for a plurality of bio-parameters from among the bio-parameters indicating the condition of the patient, displaying each of second screen displays including detailed bio-information for each of the plurality of bio-parameters for which the events occurred, on the display screen, alternately in a predetermined time interval, wherein each of the second screen displays include a tabular and graphical data of the bio-parameters for which the events occurred, on the display screen.

2. The method of claim 1, further comprising emitting a sound source when each of the plurality of events occurs, thereby notifying a user that the each of the plurality of events has occurred.

3. The method of claim 1, wherein the each of the second screen displays further includes a message notifying a user that the each of the plurality of events has occurred, on the display screen.

4. The method of claim 1, wherein
in the determining whether the plurality of events occurs, input of a signal is monitored, and
in the displaying the second screen displays, the first screen display is converted to the each of the second screen displays according to the inputted signal.

5. The method of claim 1, wherein
the basic bio-information comprises at least one selected from a time-series graph and numeric data about the bio-parameters obtained in real time, and
the detailed bio-information comprises a temporal data tendency of the basic bio-information, and the basic bio-information.

6. The method of claim 1, wherein
the bio-parameters indicating the condition of the patient are numerical, and
the displaying each of second screen displays comprises:
representing the numerical bio-parameters indicating the condition of the patient in a non-numerical display, the non-numeral display comprising a table or graph.

7. The method of claim 6, wherein the representing the numerical bio-parameters indicating the condition of the patient in a non-numerical display comprises displaying statistical data according to the time, the statistical data denoting changing over time of the bio-parameters for which the event occurred.

8. The method of claim 1, wherein the displaying each of second screen displays comprises:
displaying a textual label indicating whether the values corresponding to obtained basic bio-information are within the predetermined range of the bio-parameters when the plurality of events occurs.

9. A non-transitory computer readable recording medium including recorded thereon, a program of computer executable instructions for executing a method of displaying bio-information, the method comprising:

obtaining basic bio-information of bio-parameters indicating a condition of a patient;

displaying a first screen display including the obtained basic bio-information of the bio-parameters, on a display screen;

comparing, by a processor, a predetermined range of respective bio-parameters with values corresponding to the obtained basic bio-information of the bio-parameters;

determining for each of the respective bio-parameters, by a processor, whether a plurality of events occurs based on whether the values corresponding to the obtained basic bio-information are respectively within the predetermined ranges of the respective bio-parameters; and when the plurality of events occurs for a plurality of bio-parameters from among the bio-parameters indicating the condition of the patient, displaying each of second screen displays including detailed bio-information for each of the plurality of bio-parameters for which the events occurred, on the display screen, alternately in a predetermined time interval, wherein each of the second screen displays include a tabular and graphical data of the bio-parameters for which the events occurred, on the display screen.

10. An apparatus for displaying bio-information, the apparatus comprising:

an obtaining unit which obtains basic bio-information of bio-parameters indicating a condition of a patient;

a monitoring unit which compares a predetermined range of respective bio-parameters with values corresponding to the obtained basic bio-information of the bio-parameters, and determines for each of the respective bio-parameters whether a plurality of events occurs based on whether the values corresponding to the obtained basic bio-information are respectively within the predetermined ranges of the respective bio-parameters, and a display unit which displays a first screen display on a display screen, and displays each of second screen displays including detailed bio-information for each of the plurality of bio-parameters for which the event occurred, on the display screen, alternately in a predetermined time interval, when the plurality of events occurs for a plurality of bio-parameters from among the bio-parameters indicating the condition of the patient, wherein the first screen display includes the obtained basic bio-information of the bio-parameters indicating the condition of the patient, and wherein each of the second screen displays include a tabular and graphical data of the bio-parameters for which the events occurred, on the display screen.

11. The apparatus of claim 10, wherein the obtaining unit further obtains the predetermined range of the bio-parameters indicating the condition of the patient; and the monitoring unit comprises an event detecting unit which determines the occurrences of the plurality of events.

12. The apparatus of claim 10, further comprising a sound emitting unit which, when the each of the plurality of events occurs, emits a sound notifying a user that the each of the plurality of events has occurred.

13. The apparatus of claim 10, wherein the each of the second screen displays further including a message notifying a user that the plurality of events has occurred, on the display screen.

14. The apparatus of claim 10, further comprising an input unit which receives selection information from a user, wherein the monitoring unit obtains a signal from the input unit, and the display unit displays the each of the second screen displays, by converting the first screen display to the each of the second screen displays, in response to the signal.

15. The apparatus of claim 10, wherein the display unit displays at least one selected from a time-series graph and numeric data about one or more of the bio-parameters obtained in real time, and a temporal data tendency of the one or more of the bio-parameters.

* * * * *